United States Patent [19]

Cullis et al.

[11] 4,151,844

[45] May 1, 1979

[54] METHOD AND APPARATUS FOR SEPARATING WHOLE BLOOD INTO ITS COMPONENTS AND FOR AUTOMATICALLY COLLECTING ONE COMPONENT

[75] Inventors: Herbert M. Cullis; Almond, Anthony L., both of Silver Spring; Michael B. Uffer, Baltimore; Mirza A. Kohja; Rodolfo R. Rodgriguez, both of Columbia, all of Md.

[73] Assignee: Baxter Travenol Laboratories, Inc., Deerfield, Ill.

[21] Appl. No.: 850,624

[22] Filed: Nov. 11, 1977

[51] Int. Cl.² ............................................. A61M 5/00
[52] U.S. Cl. ............................ 128/214 R; 128/214 E; 210/74; 210/194; 210/DIG. 23
[58] Field of Search .......... 128/214 R, 214 E, 214 B; 233/10 R, 25; 210/74, 194, DIG. 23

[56] References Cited

U.S. PATENT DOCUMENTS

| | | | |
|---|---|---|---|
| 2,876,769 | 3/1959 | Cordova | 128/214 R |
| 3,489,145 | 1/1970 | Judson et al. | 128/214 R |
| 3,519,201 | 7/1970 | Eisel et al. | 128/214 R |
| 3,655,123 | 4/1972 | Judson et al. | 128/214 R X |
| 3,802,432 | 4/1974 | Djerassi | 128/214 R |
| 3,812,482 | 5/1974 | Clark | 128/214 E X |
| 3,892,236 | 7/1975 | Djerassi | 128/214 R |
| 4,086,924 | 5/1978 | Latham | 128/214 R |

Primary Examiner—Robert E. Bagwill
Attorney, Agent, or Firm—Henry W. Collins; Thomas R. Vigil; Paul C. Flattery

[57] ABSTRACT

The method, and the apparatus for carrying out the steps of the method, are utilized in the centrifugal liquid processing of whole blood wherein whole blood is withdrawn from a donor, passed through a fluid system and the blood is centrifuged to separate the same into at least three components. One component which is to be collected is withdrawn at a fixed rate of volumetric displacement while the other two components are withdrawn at variable rates of volumetric displacement. The other two components are recombined and returned to the donor. The withdrawal of the one component is optically monitored to determine whether or not either one of the other components is being mixed with the one component. When such a mixing is sensed, the rate of withdrawal of one of the other two components is increased while the rate of withdrawal of the other components is decreased thereby to ensure withdrawal of the desired one component, e.g., white blood cells with minimal contamination thereof with the other two components, e.g., red blood cells and plasma containing platelets. A given amount of the one component withdrawn is collected in a receptacle.

20 Claims, 4 Drawing Figures

METHOD AND APPARATUS FOR SEPARATING WHOLE BLOOD INTO ITS COMPONENTS AND FOR AUTOMATICALLY COLLECTING ONE COMPONENT

CROSS REFERENCE TO RELATED APPLICATIONS

This application is related to co-pending application Ser. No. 850,622, filed Nov. 11, 1977 (now U.S. Pat. No. 4,127,231) and entitled SUPPORT ARM ASSEMBLY FOR A CENTRIFUGAL LIQUID PROCESSING APPARATUS and to co-pending application Ser. No. 850,621, filed Nov. 11, 1977 (now U.S. Pat. No. 4,132,349) entitled IMPROVED ROTOR DRIVE ASSEMBLY FOR A CENTRIFUGAL LIQUID PROCESSING APPARATUS, the disclosures of which are incorporated herein by reference.

BACKGROUND OF THE INVENTION

1. Field of the Invention

The present invention relates to a method and apparatus for separating whole blood into components thereof and for automatically collecting one of the components.

2. Description of the Prior Art

Heretofore various method and apparatus have been proposed for separating whole blood into at least three components thereof in a centrifugal liquid processing apparatus where a rotor assembly having a container for receiving the whole blood to be processed by centrifugation is rotated in the apparatus to cause separation of the whole blood into red blood cells at the outer radius, a buffy coat of white blood cells at an intermediate radius and plasma containing platelets at an inner radius of the container. Outlets are provided on the container at the different radii and tubings are connected to the outlets. Pumps are provided for withdrawing each of the blood components which collects at one of the radii and at a zone adjacent each of the outlets. The outlets are coupled to the tubings either directly or by means of a fluid seal. When they are connected directly, twisting is prevented by reason of the rotor assembly being driven at a speed twice the speed of a coaxial member mounting a cable holding device through which the tubings pass to reach the bowl in the rotor assembly. As a result of the different speeds of the coaxial member and the rotor assembly, twisting is prevented. A further explanation of an apparatus having such an arrangement and operation can be found in U.S. Pat. No. 3,986,442.

As the whole blood is centrifuged, red blood cells are being withdrawn by one pump, white blood cells are withdrawn by another pump and plasma containing platelets is being withdrawn by still another pump. The rates of withdrawal by the various pumps depend upon the concentration of these components in the blood and upon changes in the radius at which these components collect during centrifugation. Since the radii at which these blood components congregate varies during centrifugation, an operator must carefully observe the blood components while they are being withdrawn. For example, when a buffy coat of white blood cells is being withdrawn, the operator must check to see that it is not too light, i.e., plasma being withdrawn with the buffy coat, or is not too dark, i.e., red blood cells being withdrawn with the buffy coat. If the buffy coat is too light or too dark the operator will then adjust the speed of a red blood cell pump in one direction and adjust the speed of a plasma pump in the opposite direction. In other words, one will be increased in speed and the other decreased in speed so that a desired composition or optical density of the buffy coat is withdrawn. This requires constant attention by an operator and is somewhat tedious when the processing extends up to an hour or more.

As will be described in greater detail hereinafter, the present invention overcomes this operator monitoring requirement by providing a method and apparatus wherein the composition or optical density of the buffy coat of white blood cells being withdrawn from a centrifuge device is automatically monitored and when changes occur therein an optical sensing device is operable to cause an adjustment in the rates of withdrawal of the red blood cells and the plasma containing platelets so as to maintain a desired composition or optical density of the white blood cells being withdrawn.

SUMMARY OF THE INVENTION

According to the invention, there is provided a method for separating whole blood into at least three blood components including the steps of: withdrawing whole blood from a donor and passing the same through a fluid system, centrifuging the blood to separate same into at least three components thereof in the fluid system, withdrawing each of the components during the centrifugation thereof, withdrawing one component at a fixed rate of volumetric displacement, withdrawing the other two components at variable rates of volumetric displacement, recombining the other two components and returning the same to the donor, sensing the withdrawal of the one component which is being withdrawn at a fixed rate to determine whether or not either one of the other components is being mixed with the one component, adjusting the rate of withdrawal of one or the other or both of the other two components in response to the sensing of a mixing of one of the other two components with the one component to ensure withdrawal of the desired one component with minimal contamination by the other two components, and collecting a given amount of the one component withdrawn.

Further according to the invention, there is provided an apparatus for separating whole blood into at least three blood components thereof comprising: means for withdrawing whole blood from a donor, a centrifuge device, means for supplying the withdrawn whole blood to the centrifuge device for the centrifugation of whole blood therein, first withdrawing means for withdrawing a first blood component from the centrifuge device, second withdrawing means for withdrawing a second blood component from the centrifuge device and third withdrawing means for withdrawing a third blood component from the centrifuge device, means for recombining the first and third blood components and returning the same to the donor, means for sensing the composition of the second blood component withdrawn, means for adjusting the rates of withdrawal of the first and third withdrawing means when a mixing of one or the other of said first and third components with the second component is sensed by said sensing means and means for collecting the second blood component.

DESCRIPTION OF THE PREFERRED EMBODIMENT

Figure 1:
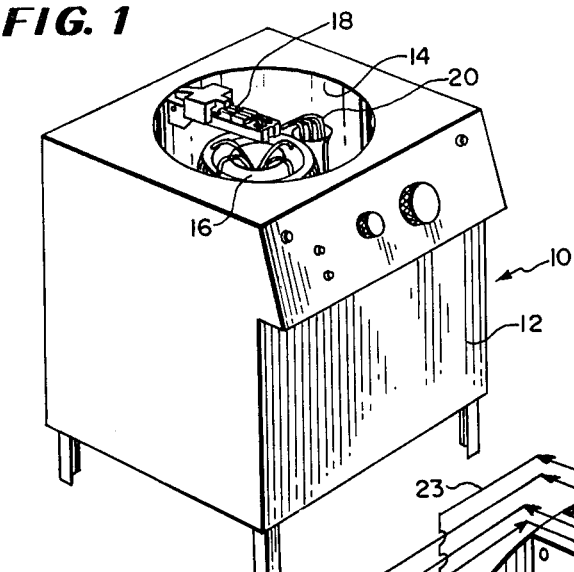
FIG. 1 is a perspective view of the centrifugal liquid processing apparatus of the present invention.

Referring to the drawings in greater detail there is generally illustrated in FIG. 1 a centrifugal liquid processing apparatus 10 for separating whole blood into components thereof. The apparatus 10 includes a cabinet 12 having a generally cylindrical opening 14 in the top thereof in which is situated a centrifuge device 16. Extending from an inner wall of the cylindrical opening 14 is a support arm assembly 18, the outer end of which is located over and centrally of the centrifuge device 16. A group 20 of four flexible tubings extend through the outer end of the arm assembly 18 for connection to the centrifuge device 16.

Figure 2:
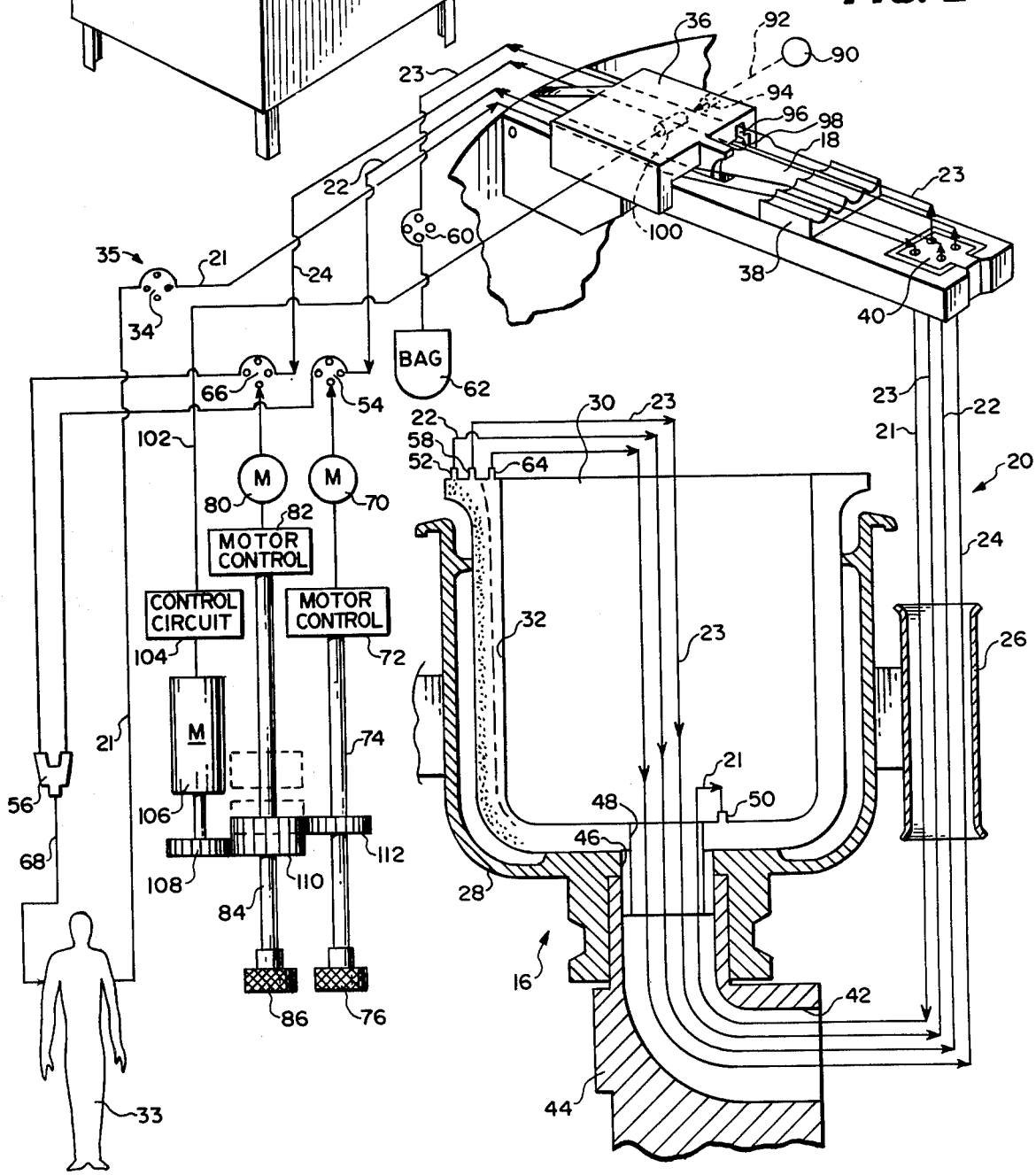
FIG. 2 is a schematic diagram of the fluid system of the apparatus shown in FIG. 1 and of the electro-mechanical control system for the apparatus including fragmentary views of portions of the apparatus.

As best shown in FIG. 2, the group 20 of the tubings comprises four tubings 21, 22, 23 and 24 which extend from the arm assembly 18 through a tubular sleeve 26 mounted to the side of a container holding receptacle 28 of the centrifuge device 16. Mounted in the centrifuge device 16 is a closed bowl 20 having a hollow interior 32 in which whole blood is centrifuged as will be described hereinafter in greater detail.

Referring to FIG. 2, the first tubing 21 is coupled in a conventional manner to a donor 33 and passed over and forms part of a peristaltic pump 34 which is operable to withdraw whole blood from the donor 33. Although not shown, it will be understood that suitable low and high pressure sensors are provided in the tubing 21 to sense high and low pressure conditions indicating a leak in the fluid system of the apparatus 10, which system is generally identified by reference numeral 35, or an occluded vein in the donor 33. When such a condition is sensed, the low and/or high pressure sensors are then operative to stop operation of the apparatus 10.

After leaving the peristaltic pump 34, the tubing 21 is directed into the apparatus 10 and onto the arm assembly 18 beneath a latch member 36 which is part of and which holds the arm assembly 18 in place and at the same time holds the tubings 21–23 on the arm assembly 18. From there the tubing 21 is trained over a tubing guide member 38 mounted on the arm assembly 18 and then through an aperture in a tubing holder 40 located at the outer end of the arm assembly 18. Then the tubing 21 passes through the tubular sleeve 26 and into a passageway 42 formed in a drive shaft 44 of a rotor drive assembly for the centrifuge device 16.

As shown, the passageway 42 is L-shaped and extends from a side of the drive shaft 44 radially inwardly and axially upwardly of the drive shaft 44 and into mating engagement with an opening 46 in the container holding receptacle 28 and through a mating opening 48 into the bottom of the bowl 30 where it connects to an inlet 50 to the hollow interior 32 of the bowl 30.

Within the bowl 30 red blood from the donor is centrifuged upon rotation of the bowl 30 with red blood cells collecting at an outer radius, a buffy coat of white blood cells collecting at an intermediate radius, and plasma with platelets therein collecting at an inner radius within the hollow portion 32 of the bowl 30. An outlet 52 is provided on the upper rim of the bowl 30 at the outer radius and adjacent a zone where the red blood cells collect. The second tubing 22 is connected to this outlet 52 and extends therefrom through the passages 48 and 42, the sleeve 26, the apertured holder 40, over guide member 38 under the latch member 36 and then over and forming a part of a peristaltic pump 54 and from there to a Y-coupling 56.

In like manner the third tubing 23 is connected to an outlet 58 on the upper rim of the bowl 30 at the intermediate radius and adjacent a zone where a buffy coat of white blood cells collects in the hollow interior 32 of the bowl 30. The tubing 23 then passes through the passages 48 and 42 through the sleeve 26, the apertured holder 40, over guide member 38 and underneath the latch member 36 and then over and forming part of a peristaltic pump 60 to a white blood cell collection bag or receptacle 62.

Again, in like manner, the fourth tubing 24 is connected to an outlet 64 located on the upper rim of the bowl 30 at an inner radius where plasma collects. From there the tubing 24 extends through the passages 48 and 42, the sleeve 26, the apertured holder 40, over the guide member 38, under the latch member 36 and then over and forming part of a peristaltic pump 66 from which the tubing 24 extends to the Y-coupling 56 where plasma and red blood cells are recombined and returned via a tubing 68 to the donor 33.

As shown, the peristaltic pump 54 is driven by a motor 70, the speed of which is controlled by a motor control 72 which is operated by a rotatable control rod 74 having a knob 76 on the outer end thereof for manual operation of the motor control 72. Typically, the motor control 72 will include an adjustable potentiometer which has a rotating sweep arm that is rotatably coupled to the rod 74 such that rotation of the knob 76 will cause adjustment of the potentiometer thereby to cause the motor control 72 to change the speed of the motor 70 for changing the speed of the pump 54.

Likewise, the peristaltic pump 66 is driven by a motor 80, the speed of which is controlled by a motor control 82 having a rod 84 extending therefrom. The rod 84 also has a knob 86 at the outer end thereof. In a similar manner to the motor control 72, the motor control 82 has a potentiometer with a rotating sweep arm which is rotatably coupled to the rod 84 such that rotation of the knob 86 will adjust the setting of the potentiometer to cause the motor control 82 to change the speed of the motor 80 and thereby the speed of the pump 66.

In accordance with the teachings of the present invention a light source 90 and a light (fiber optic) pipe 92 transmit light from the light source 90 to a passageway 94 in the latch member 36. The passageway 94 opens into a groove 96 in the latch member 36, which groove is aligned with a boss 98 mounted on the arm assembly 18. The boss 98 holds the light transmissive portion of the tubing 23 in the groove 96 so that light entering the passageway 94 is passed through the light transmissive portion of the tubing 23 to a light pickup device 100 in an aligned passageway 101 in the latch member 36 so that the optical density of the white blood cells being withdrawn through the tubing 23 can be sensed and monitored by light pickup device 100.

The light pickup device 100 can be a fiber optic pipe or can be a sensor with an electrical conductor leading therefrom. In either event there is illustrated in FIG. 2 a line 102 from the light pickup device 100 which can be a continuance of the device 100, namely, a fiber optic light pipe or which can be an electrical conductor, either of which is connected to a control circuit 104. As will be described in greater detail hereinafter, the control circuit 104 is operable to drive a gear drive motor 106 which is connected to a gear 108. The gear 108 is adapted to mesh with a gear 110 on the rod 84 which in turn meshes with a gear 112 on the rod 76 as shown in FIG. 2.

The control circuit 104 determines whether or not the light (optical density) received by the light pickup device 100 is within a predetermined range and whether or not the optical density is increasing or decreasing. Then, depending upon the optical density sensed and whether it is increasing or decreasing the control circuit 104 will cause various rotations of the motor 106 and gear 108, thereby to cause the gear 110 to rotate in a clockwise or counterclockwise direction which in turn will cause the gear 112 to rotate in a counterclockwise or clockwise direction. Such rotations of the gears 110 and 112 will cause an adjustment of the potentiometers in the motor control circuits 82 and 72 to effect corresponding changes, but in opposite directions, in the speeds of the motors 70 and 80. In this respect, when the speed of motor 80 is increased or decreased, the speed of the motor 70 is decreased or increased.

Briefly, summarizing the operation of the electromechanical system of the apparatus 10, which system is generally identified by reference numeral 113, when the density of the buffy coat of white blood cells being withdrawn darkens beyond a predetermined range, defining a desired composition of the buffy coat being withdrawn, the control circuit 104 will cause the speed of motor 70 to be increased and the speed of motor 80 to be decreased so that more red blood cells and less plasma are withdrawn from the bowl 30. In this way the zone containing the desired composition of a buffy coat of white blood cells is maintained at the radius of the outlet 58.

In like manner when the optical density of the buffy coat sensed is below the predetermined range indicating that more plasma is in the buffy coat than is desired, the control circuit 104 will cause the motor 106 to rotate the gear 108 so as to cause the motor control 82 to increase the speed of the motor 80 and the motor control 72 to decrease the speed of the motor 70 thereby to withdraw more plasma and less red blood cells and maintain the zone of the buffy coat having the desired composition of white blood cells at the radius of the outlet 58.

To provide greater flexibility in the apparatus 10 the rod 84 is axially movable between three positions, the first position being that shown solid in FIG. 2 where the gear 110 engages the gear 108 and the gear 112. In a second position, the rod 84 is moved inwardly toward the motor control 82 to a position where the gear 100 shown in phantom lines does not engage the gear 108 but only the gear 112. In this position, only manual adjustment of the speeds of the pumps 54 and 66 can be effected and in this position adjustment of one knob 86 causes an equal adjustment but in the opposite direction of the other knob 76.

In the third position, the gear 110, again shown in phantom lines, does not engage either of the gears 108 or 112. In this position, the speed of the pumps 54 and 66 and the respective rates of withdrawal of fluids through the tubings 22 and 24 are each controlled separately by the knobs 86 and 76.

Figure 3:
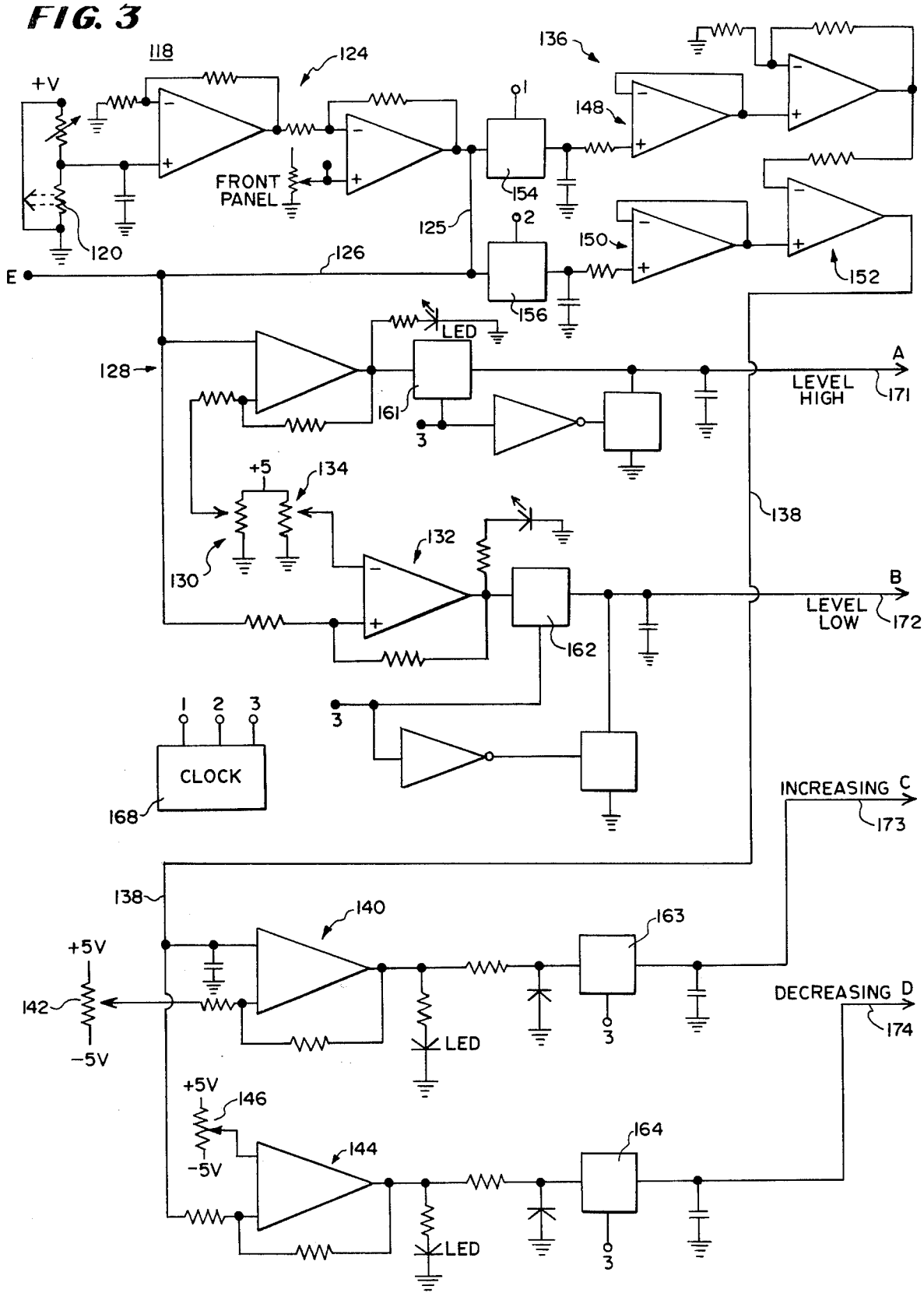
FIG. 3 is a schematic circuit diagram of an analog portion of the control circuit shown in FIG. 2.

Referring now to FIG. 3, there is illustrated therein an analog circuit 118 of the control circuit 104. The analog circuit 118 includes a phototransistor 120 which receives light from the light pickup device 100, or the phototransistor 120 can be incorporated into the light pickup device 100. The signal generated by the phototransistor 120 is amplified by an amplifying circuit 124 and then applied via conductors 125 and 126 to a first comparing circuit 128 which compares the amplified signal with a reference voltage established by a voltage divider 130. This is a high level voltage for determining the upper level of the predetermined range of optical density. The amplified signal is also applied to a second comparing circuit 132 which compares the output signal with a low level voltage established by a potentiometer 134.

The amplified signal at the output of the amplifier circuit 124 is also applied to a differentiator circuit 136. The output from the differentiator circuit 136 is then supplied via a conductor 138 to a third comparing circuit 140 which compares the differentiated output signal with a high reference voltage established by a voltage divider 142. The same output signal from the differentiator circuit 136 is also supplied to a fourth comparing circuit 144 which compares said signal to a low reference voltage established by a voltage divider 146.

The differentiator circuit 136 includes a first sample and hold circuit 148, a second sample and hold circuit 150 and a comparator circuit 152. The outputs of the sample and hold circuits 148 and 150 are supplied to the comparator circuit 152.

Coupled to the input to the first sample and hold circuit 148 is a first gate 154 and coupled in the input to the second sample and hold circuit 150 is a second gate 156. Also, in the outputs of all four comparing circuits 128, 132, 140 and 144 are gates 161, 162, 163 and 164.

The analog circuit 118 also includes a clock 168 with a first output 1, a second output 2, and a third output 3. The first output 1 is coupled to the first gate 154, the second output 2 is coupled to the second gate 156 and the third output 3 is coupled to the gates 161–164 coupled in the outputs of the comparing circuits 128, 132, 140 and 144 leading to signal output conductors 171–174.

In the operation of the analog circuit illustrated in FIG. 3, gate 154 is closed by a short pulse from output 1 of clock 168 at a first point in time to make a first sampling of the amplified signal which is stored in the first sample and hold circuit 148. At a second point in time, approximately 1 minute later, another short pulse appears on the second output 2 of the clock for closing the gate 156 for a short period of time to place a second sampling of the amplified signal appearing at a later point in time into the second sample and hold circuit 150. The comparator circuit 152 will then compare the outputs of the sample and hold circuits 148 and 150 and determine whether there has been an increase or decrease in the amplified signal. If there has been an increase, the comparator circuit 152 will produce a high level signal which will be sensed by the third comparing circuit 140 to produce a high logic output signal to be supplied to conductor 173. If the amplified signal had decreased, the comparator circuit 152 will produce a low output signal which will be sensed by the fourth comparing circuit 144 which will then produce a high logic output signal to be supplied to conductor 174.

Figure 4:
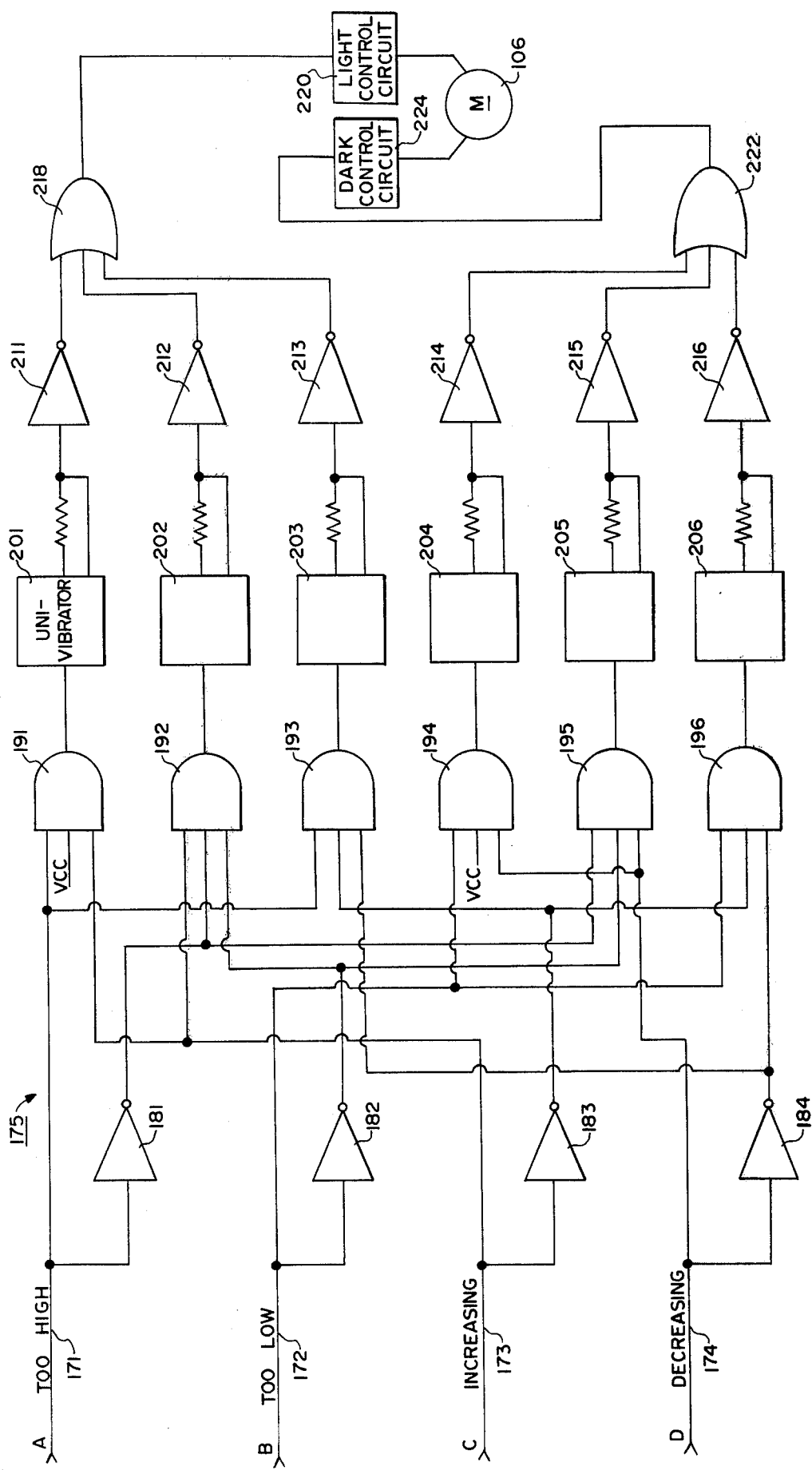
FIG. 4 is a schematic circuit diagram of a digital portion of the control circuit shown in FIG. 2.

Shortly after the second gate 156 is closed a gating pulse from output 3 is supplied to the gates 161, 162, 163 and 164 so that all signal levels can now be applied to a digital circuit by the control circuit 104 shown in FIG. 4 and generally identified by reference numeral 175.

Turning now to FIG. 4, the digital circuit 175 comprises four inverters 181-184 which are coupled to each one of the output conductors 171, 172, 173 and 174 from the four comparing means 128, 132, 140 and 144. The digital circuit 175 also includes six AND circuits 191-196. As shown, the outputs from the comparing circuits 128, 132, 140 and 144 and the outputs from the inverters 181-184 are coupled to the various AND circuits 191-196. The output from each of the AND circuits 191-196 is coupled to one of the six univibrator circuits 201-206. The output of the first three univibrator circuits 201-203 are supplied respectively to three inverters 211, 212 and 213. Similarly, the outputs of the univibrator circuits 204, 205 and 206 are supplied respectively to three inverter circuits 214, 215 and 216. As shown, the outputs from the inverters 211-213 are supplied to an OR circuit 218 which feeds a so-called "light" control circuit 220 coupled to gear drive motor 106. The control circuit 220 is referred to as a "light" control circuit since the phototransistor 120 will provide a high level signal on conductor 171 when the optical density of the buffy coat of white blood cells is low indicating a mixing of plasma with the buffy coat, and when such a signal is passed by the OR circuit 181 to the control circuit 120, the "light" control circuit 120 will then be operative to cause the gear drive motor 106 to decrease the speed of the motor 70 controlling the pumping of red blood cells while increasing the speed of the motor 80 controlling the pumping of plasma thereby to increase the optical density of the buffy coat being sensed.

Likewise, the outputs of the inverter circuits 214–216 are supplied to an OR circuit 222, the output of which is coupled to a so-called "dark" control circuit 224. This "dark" control circuit 224 will be operative when a "low" signal indicating a high optical density is passed through the OR circuit 222 to the "dark" control circuit 224. This signal will cause the control circuit 224 to increase the speed of the motor 70 for the pump 54 for pumping red blood cells and to decrease the speed of the motor 80 controlling the pump 66 for pumping plasma, thereby to decrease the density of the buffy coat being sensed and withdrawn from the bowl 30.

The univibrators 201-204 and univibrators 204-206 have different output pulse widths to cause different speed correction. In this respect, the univibrator 201 produces the largest width output pulse for causing the largest rotation of the motor 106 for decreasing the speed of pump 54 pumping of red blood cells. The univibrator circuit 202 produces a pulse of an intermediate width for producing an intermediate rotation of the motor 106 to cause an intermediate decrease in the speed of the pump 54 and the univibrator circuit 203 produces the smallest width impulse for causing a small rotation of the motor 106 to cause a small decrease in the speed of the pump 54.

In a similar manner univibrator 204 produces a large width pulse, univibrator 205 produces an intermediate width pulse and univibrator 206 produces a small width pulse which pulses cause a large, intermediate and small rotation of the motor 106 respectively, thereby to cause a large, intermediate or small increase in the speed of the pump 54 which is withdrawing red blood cells from the bowl 30.

It is to be understood that for each decrease or increase in the speed of the pump 54 for pumping red blood cells, there is, by reason of the meshing engagement between the gears 108, 110 and 112, a simultaneously corresponding decrease or increase in the speed of the pump 66 for withdrawing plasma containing platelets from the bowl 30.

It will be apparent from a study of the circuit connections of the digital circuit 175 in FIG. 4 that such digital circuit 175 will operate in the following manner to adjust the rates of withdrawal of red blood cells and plasma in response to different sensings:

A. When the optical density sensed is above the predetermined range and is increasing, a large decrease in the rate of withdrawal of the red blood cells is effected with a corresponding increase in the rate of withdrawal of plasma;

B. When the optical density is within the predetermined range but is increasing, an intermediate reduction in the rate of withdrawal of the red blood cells is effected with a corresponding increase in the rate of withdrawal of the plasma;

C. When the optical density is not increasing but is above the predetermined range, a minimum decrease in the rate of withdrawal of the red blood cells is effected with a corresponding increase in the rate of withdrawal of plasma;

D. When the optical density is below the predetermined range and is decreasing, a large increase in the withdrawal of red blood cells is effected with a corresponding decrease in the withdrawal of plasma;

E. When the optical density is below the predetermined range but is not changing, an intermediate increase in withdrawal of red blood cells is effected with a corresponding decrease in the withdrawal of plasma;

F. When the optical density is below the predetermined range but is not changing, a minimum increase in the rate of withdrawal of red blood cells is effected with a corresponding decrease in the rate of withdrawal of plasma.

From the foregoing description it will be apparent that the method and apparatus of the present invention provide for an automatic and effective collection of white blood cells. Also, it will be apparent to those skilled in the art that obvious modifications and variations can be made to the method and apparatus of the present invention without departing from the teachings of the invention. Accordingly, the scope of the invention is only to be limited as necessitated by the accompanying claims.

We claim:

1. A method for separating whole blood into at least three blood components including the steps of: withdrawing whole blood from a donor and passing the same through a fluid system, centrifuging the blood to separate same into at least three components thereof in the fluid system, withdrawing each of the components during the centrifugation thereof, withdrawing one component at a fixed rate of volumetric displacement, withdrawing the other two components at variable rates of volumetric displacement, recombining the other two components and returning the same to the donor, sensing the withdrawal of the one component which is being withdrawn at a fixed rate to determine whether or not either one of the other components is being mixed with the one component, adjusting the rate of withdrawal of one or the other or both of the other two components in response to the sensing of a mixing of one of the other two components with the one component to ensure withdrawal of the desired one component with minimal contamination by the other two components, and collecting a given amount of the one component withdrawn.

2. The method according to claim 1 wherein the three components are (1) plasma and platelets, (2) a buffy coat of white blood cells and (3) red blood cells and wherein the desired component being withdrawn is white blood cells.

3. The method according to claim 2 wherein said sensing is accomplished by passing a light through a light transmissive portion of a tubing through which the white blood cells are being withdrawn from the area of centrifugation of the whole blood and sensing the light passed through the light transmissive portion of the tubing to determine the optical density of the white blood cells being withdrawn, increasing or decreasing the rate of withdrawal of the red blood cells while at the same time decreasing or increasing the rate of withdrawal of the plasma dependent upon the amount of light sensed above or below a predetermined range indicative of a desired optical density of the white blood cells being withdrawn, sensing whether the optical density of the white blood cells being withdrawn is increasing or decreasing and causing varying amounts of adjustments in the rates of withdrawal of red blood cells and plasma dependent upon whether or not the optical density sensed is above or below the said predetermined range and whether or not the optical density is increasing or decreasing.

4. The method according to claim 3 wherein said adjusting of the rates of withdrawal of red blood cells and plasma in response to different sensings is accomplished in the following manner:

A. When the optical density sensed is above the predetermined range and is increasing, a large decrease in the rate of withdrawal of the red blood cells is effected with a corresponding increase in the rate of withdrawal of plasma;

B. When the optical density is within the predetermined range but is increasing, an intermediate reduction in the rate of withdrawal of the red blood cells is effected with a corresponding increase in the rate of withdrawal of the plasma;

C. When the optical density is not increasing but is above the predetermined range, a minimum decrease in the rate of withdrawal of the red blood cells is effected with a corresponding increase in the rate of withdrawal of plasma;

D. When the optical density is below the predetermined range and is decreasing a large increase in the withdrawal of red blood cells is effected with a corresponding decrease in the withdrawal of plasma;

E. When the optical density is below the predetermined range but is not changing, an intermediate increase in withdrawal of red blood cells is effected with a corresponding decrease in the withdrawal of plasma;

F. When the optical density is below the predetermined range but is not changing, a minimum increase in the rate of withdrawal of red blood cells is effected with a corresponding decrease in the rate of withdrawal of plasma.

5. The method according to claim 1 wherein said sensing is accomplished by passing a light through a light transmissive portion of tubing through which the one component is being withdrawn from the area of centrifugation of the whole blood and sensing the light passed through the light transmissive portion of the tubing to determine the composition of the one component being withdrawn and adjusting the rate of withdrawal of one or the other or both of the other two blood components depending upon the amount of light sensed above or below a predetermined range indicative of the desired composition of the one blood component being withdrawn.

6. The method according to claim 1 wherein said rates of withdrawal for withdrawing each of the other two blood components respectively are adjusted simultaneously when a mixture of one or the other of the two other components is sensed, mixed with the one component, and such simultaneous adjustments are inverse to each other such that when the rate of withdrawal of one of the two other components is increased, the rate of withdrawal of the other of the two other components is automatically decreased.

7. An apparatus for separating whole blood into at least three blood components thereof comprising: means for withdrawing whole blood from a donor, a centrifuge device, means for supplying the withdrawn whole blood to the centrifuge device for the centrifugation of whole blood therein, first withdrawing means for withdrawing a first blood component from the centrifuge device, second withdrawing means for withdrawing a second blood component from the centrifuge device and third withdrawing means for withdrawing a third blood component from the centrifuge device, means for recombining the first and third blood components and returning the same to the donor, means for sensing the composition of the second blood component withdrawn, means for adjusting the rates of withdrawal of the first and third withdrawing means when a mixing of one of the other of said first and third components with the second component is sensed by said sensing means and means for collecting the second blood component.

8. The apparatus according to claim 7 wherein said means for sensing the composition of the second blood component withdrawn includes a light source for passing light through a light transmissive portion of a tubing through which the second blood component is withdrawn and light pickup means including an optical sensor for sensing the amount of light transmitted through said light transmissive portion of said tubing.

9. The apparatus according to claim 8, wherein said first withdrawing means includes a first pump driven by a first motor and a first motor control means for operating said first motor, said second withdrawing means includes a second motor driven pump operated by a second control means at a fixed speed, said collection means includes a receptacle connected to the output of said second pump, said third withdrawing means includes a third pump, a third motor for driving same and a third motor control means for operating said third motor and said rate of withdrawal adjusting means includes control circuit means coupled to said first and third motor control means, said sensing means being coupled to said control circuit means which is operative in response to the amount of light sensed by said sensing means to adjust said first and third motor control means for adjusting the speeds of said first and third pumps.

10. The apparatus according to claim 9 wherein said first motor control means includes an electrical speed control circuit having a rotatable mechanical control for adjusting the speed of said first motor, a first rotatable control rod extending from said mechanical control and having a first gear mounted thereon, a gear drive motor having a second gear on an output shaft thereof, said control circuit means being connected to said gear drive motor, said third motor control means including an electrical speed control circuit having a rotatable mechanical control for adjusting the speed of the third motor and a second rotatable control rod extending from said mechanical control, a third gear mounted on said second control rod and adapted to engage said first and second gears, said control circuit means being operative in response to the amount of light sensed by said sensing means to cause said gear drive motor to rotate said second gear in either a clockwise or a counter-clockwise direction for a given arcuate distance thereby to rotate said third gear in one direction and by reason of said meshing engagement between said third gear and said first gear to also rotate said first gear but in the opposite direction, thereby to adjust the speed of said first motor control means to cause the first motor to increase or decrease the speed of the first pump while simultaneously adjusting the speed of said third motor to decrease or increase the speed of said third pump so that a desired composition of the second component, i.e., buffy coat is withdrawn by said second pump.

11. The apparatus according to claim 10 wherein said first control rod has a first knob on the outer end thereof for manually operating said first motor control means, and said second control rod has a second knob on the outer end thereof for manually operating said second motor control means, said second control rod also being axially movable between three positions, the first position being where said third gear engages both said first gear and said second gear, the second position being where said third gear only engages said first gear and a third position where said third gear does not engage said first gear or said second gear, so that, in the first position, control of the speed of the first and third pumps is automatic and determined and controlled by said sensing means, and in the second position, control of the speed of the first and third pumps is achieved manually with adjustment of one of said knobs causing adjustment of the other knob in the reverse direction and, in the third position, said first motor control means and said third motor control means are controlled independently by said knobs.

12. The apparatus according to claim 7 wherein said means for supplying whole blood to the centrifuge device includes a first tubing which is coupled to the donor and extends into said centrifuge device for delivering whole blood to said centrifuge device, said first withdrawing means includes a second tubing which is coupled to an outlet of said centrifuge device located adjacent a zone where red blood cells collect in said centrifuge device, said second tubing extending out of the said centrifuge device for returning red blood cells to the donor, said second withdrawing means includes a third tubing which is connected to an outlet of said centrifuge device located adjacent a zone where a buffy coat of white blood cells collects in said centrifuge device, said third tubing extending out of said centrifuge device and being coupled to said collection means, and said third withdrawing means includes a fourth tubing which is coupled to an outlet of said centrifuge device adjacent a zone where plasma and platelets collect in said centrifuge device, said fourth tubing extending out of said centrifuge device and being coupled to said second tubing for recombining red blood cells, platelets and plasma for return to the donor.

13. The apparatus according to claim 12 including a support arm, said four flexible tubings being supported by and held on said support arm and extending therefrom into said centrifuge device.

14. The apparatus according to claim 13 including a light source, means for directing light from said light source to a location on said support arm adjacent a light transmissive portion of said third tubing, light pickup means on said support arm on the other side of said light transmissive portion of said tubing and in line with said light directing means, said light pickup means including said sensing means which is operative to generate an electrical signal which is supplied to said rate of withdrawal adjusting means.

15. The apparatus according to claim 14, wherein said first withdrawing means includes a first pump driven by a first motor and a first motor control means for operating said first motor, said second withdrawing means includes a second motor driven pump operated by a second control means at a fixed speed, said collectijn means includes a receptacle connected to the output of said second pump, said third withdrawing means includes a third pump, a third motor for driving same and a third motor control means for operating said third motor and said rate of withdrawal adjusting means includes control circuit means coupled to said first and third motor control means, said sensing means being coupled to said control circuit means which is operative in response to the amount of light sensed by said sensing means to adjust said first and third motor control means for adjusting the speeds of said first and third pumps.

16. The apparatus according to claim 15 wherein said first motor control means includes an electrical speed control circuit having a rotatable mechanical control for adjusting the speed of said first motor, a first rotatable control rod extending from said mechanical control and having a first gear mounted thereon, a gear drive motor having a second gear on an output shaft thereof, said control circuit means having connected to said gear drive motor, said third motor control means including an electrical speed control circuit having a rotatable mechanical control for adjusting the speed of the third motor and a second rotatable control rod extending from said mechanical control, a third gear mounted on said second control rod and adapted to engage said first and second gears, said control means being operative in response to the amount of light sensed by said sensing means to cause said gear drive motor to rotate said second gear in either a clockwise or a counter-clockwise direction for a given arcuate distance thereby to rotate said third gear in one direction and by reason of said meshing engagement between said third gear and said first gear to also rotate said first gear but in the opposite direction, thereby to adjust the speed of said first motor control means to cause the first motor to increase or decrease the speed of the first pump while simultaneously adjusting the speed of said third motor to decrease or increase the speed of said third pump so that a desired composition of the second component, i.e., buffy coat is withdrawn by said second pump.

17. The apparatus according to claim 16 wherein said sensing means is operative to generate an electrical signal and said control means includes amplifying means for amplifying said electrical signal, first comparing means for comparing the amplified signal with a first reference voltage and operable to produce a logic output signal when the amplified signal exceeds the first reference voltage, second comparing means for comparing said amplified signal with a second reference voltage and for generating a logic output signal when said amplified signal is lower than said second reference voltage, differentiating means for differentiating said amplified signal over a period of time to determine whether it is increasing or decreasing and for producing a low logic signal when the amplified signal is decreasing over a period of time and a high logic signal when the amplified signal is increasing over a period of time, third comparing means for comparing said differential output signal with a third reference voltage and for producing a logic output signal indicating said amplified signal is increasing, fourth comparing means for comparing said differential output signal with a fourth reference voltage and for producing a logic output signal when said amplified signal is decreasing and digital circuit means coupled to the outputs of said four comparing means for producing a plurality of output signals, said digital circuit means having two outputs, one output being connected to a first electronic device for causing said gear drive motor to rotate in one direction and another output being connected to a second electronic device for causing said gear drive motor to rotate in the opposite direction said digital circuit means being operable to provide six control signals dependent upon the signals received from said four comparing means, three signals appearing on said first output and being reduce speed signals which cause rotation of said second gear different amounts in one direction, such as a large rotation, an intermediate rotation or a small rotation to cause a desired reduction in speed of said first pump and a corresponding increase in speed of said third pump, and the other three signals being increase speed signals which cause rotation of said second gear different amounts in the opposite direction, such as a large rotation, an intermediate rotation, or a small rotation to cause a desired increase in speed of said first pump and a corresponding decrease in speed of said third pump, the particular control signal generated being dependent upon whether a high signal or a low signal is sensed by said first or second comparing means and dependent upon whether an increasing amplified signal or decreasing amplified signal is sensed by said third or fourth comparing means.

18. The apparatus according to claim 17, wherein said differentiating means includes a first sample and hold circuit for sampling said amplified signal at one point in time and a second sample and hold circuit for sampling said amplified signal at a second point of time, the outputs of said sample and hold circuits being coupled to fifth comparing means which is operable to generate a high logic signal when the amplified signal is increasing, a low logic signal when the amplified signal is decreasing, and a zero value signal when there has been no change in the amplified signal.

19. The apparatus according to claim 18 including a first gate in the input to said first sample and hold circuit, a second gate in said input to said second sample and hold circuit, gating means in the output of each of said first, second, third and fourth comparing means, and gate signal generating means operable cyclically to generate a first gating signal which is supplied to said first gate to open said first gate at a first point in time, a second gating signal which is supplied to said second gate to open said second gate at a second point in time and a third gating signal which is supplied to said gating means in the outputs of said first, second, third and fourth comparing means at a third point in time.

20. The apparatus according to claim 17 wherein said digital circuit means includes inverter circuits which are coupled to the outputs of said four comparing means, AND circuit means coupled to said inverter circuits and to said comparing means, said AND circuit means comprising six AND circuits each of which is coupled to a univibrator circuit, said first, second and third univibrator circuits being coupled to a first OR circuit which is coupled to a first control circuit for causing the gear drive motor to rotate in a direction which will cause the speed of the first pump for pumping red blood cells to be decreased, said first univibrator circuit providing a pulse which causes a large rotation of said gear drive motor to cause a large decrease in the speed of said first pump, said second univibrator circuit providing a pulse which causes an intermediate rotation of said gear drive motor to cause an intermediate reduction in the speed of said first pump and said third univibrator circuit providing a pulse which causes a small decrease in the rotation of the gear drive motor to cause a small decrease in the speed of said first pump, and said fourth, fifth and sixth univibrator circuits being coupled to a second control circuit for increasing the speed of said first pump, said fourth univibrator circuit providing a pulse which causes a large rotation of said gear drive motor to cause a large increase in the speed of rotation of said first pump, said fifth univibrator circuit providing a pulse which causes an intermediate rotation of said gear drive motor to cause an intermediate increase in the speed of said first pump and said sixth univibrator circuit providing a pulse which causes a small increase in the speed of said first pump, for each said change in speed of said first pump said third pump is rotated an equal amount but in the opposite direction by reason of said meshing engagement between said first, second and third gears.

* * * * *

UNITED STATES PATENT AND TRADEMARK OFFICE
CERTIFICATE OF CORRECTION

PATENT NO. : 4,151,844
DATED : May 1, 1979
INVENTOR(S) : Herbert M. Cullis et al.

It is certified that error appears in the above-identified patent and that said Letters Patent are hereby corrected as shown below:

Column 12, line 12, after the first-mentioned "said" insert --third--.

Column 12, line 41, after "means", delete "having" and insert --being--.

Column 12, line 48, after "control" insert --circuit--.

Signed and Sealed this

Fourth Day of December 1979

[SEAL]

Attest:

SIDNEY A. DIAMOND

Attesting Officer

Commissioner of Patents and Trademarks